(12) United States Patent
Elbert

(10) Patent No.: US 10,478,153 B2
(45) Date of Patent: *Nov. 19, 2019

(54) SYSTEM AND METHOD FOR MONITORING DEVICE ENGAGEMENT

(71) Applicant: ACIST Medical Systems, Inc., Eden Prairie, MN (US)

(72) Inventor: Arcadi Elbert, Sunnyvale, CA (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 722 days.

This patent is subject to a terminal disclaimer.

(21) Appl. No.: 15/206,394

(22) Filed: Jul. 11, 2016

(65) Prior Publication Data

US 2016/0317120 A1  Nov. 3, 2016

Related U.S. Application Data

(63) Continuation of application No. 13/894,045, filed on May 14, 2013, now Pat. No. 9,414,812.

(51) Int. Cl.
*A61B 8/12* (2006.01)
*A61B 8/00* (2006.01)
*A61M 25/01* (2006.01)

(52) U.S. Cl.
CPC ............. *A61B 8/12* (2013.01); *A61B 8/4209* (2013.01); *A61B 8/4461* (2013.01); *A61B 8/461* (2013.01);

(Continued)

(58) Field of Classification Search
CPC .... A61B 8/12; A61B 8/54; A61B 8/58; A61B 8/4209; A61B 8/4461; A61B 8/461; A61M 25/0113

(Continued)

(56) References Cited

U.S. PATENT DOCUMENTS 4,708,125 A  11/1987 Miketic et al.
4,753,248 A  6/1988 Engler et al.
(Continued)

FOREIGN PATENT DOCUMENTS

CN  102264306 A  11/2011
JP  2009515606 A  4/2009
(Continued)

OTHER PUBLICATIONS

European Patent Application No. 17152364.0, Extended European Search Report dated Mar. 14, 2017, 10 pages.

(Continued)

*Primary Examiner* — Oommen Jacob
(74) *Attorney, Agent, or Firm* — Fredrikson & Byron, P.A.

(57) ABSTRACT

An intravenous ultrasound (IVUS) system can include a catheter and a translation mechanism for translating the catheter. Engagement between the catheter and the translation mechanism may be detected, and the translation mechanism can be placed in a connected or disconnected mode, accordingly. When in connected mode, certain IVUS operations may be enabled when compared to disconnected mode, wherein such operations may be disabled. Thus, some embodiments may ensure proper engagement between the catheter and the translation mechanism prior to allowing certain IVUS operations to be carried out.

20 Claims, 8 Drawing Sheets

(52) U.S. Cl.
CPC .................. *A61B 8/54* (2013.01); *A61B 8/58* (2013.01); *A61M 25/0113* (2013.01); *A61B 2560/0266* (2013.01); *A61B 2560/0276* (2013.01); *A61B 2562/228* (2013.01)

(58) Field of Classification Search
USPC ................ 600/459, 462, 466, 467, 438, 407
See application file for complete search history.

(56) References Cited

U.S. PATENT DOCUMENTS

| | | | |
|---|---|---|---|
| 5,149,322 A * | 9/1992 | Nash | A61B 17/320758 604/110 |
| 5,361,768 A | 11/1994 | Webler et al. | |
| 5,485,846 A | 1/1996 | Webler et al. | |
| 5,592,942 A | 1/1997 | Webler et al. | |
| 5,759,153 A | 6/1998 | Webler et al. | |
| 5,827,313 A | 10/1998 | Ream et al. | |
| 5,957,941 A | 9/1999 | Ream | |
| 6,004,271 A | 12/1999 | Moore et al. | |
| 6,013,030 A | 1/2000 | Webler et al. | |
| 6,290,675 B1 | 9/2001 | Vujanic et al. | |
| 6,292,681 B1 | 9/2001 | Moore | |
| 6,398,755 B1 | 6/2002 | Belef et al. | |
| 6,974,465 B2 | 12/2005 | Belef et al. | |
| 7,686,816 B2 | 3/2010 | Belef et al. | |
| 7,988,633 B2 | 8/2011 | Hossack et al. | |
| 8,104,479 B2 | 1/2012 | Glynn et al. | |
| 8,414,505 B1 | 4/2013 | Weitzner et al. | |
| 8,459,266 B2 | 6/2013 | Glynn et al. | |
| 8,627,823 B2 * | 1/2014 | Glynn | A61B 8/12 128/853 |
| 9,084,532 B2 | 7/2015 | Horiike | |
| 9,414,812 B2 * | 8/2016 | Elbert | A61B 8/54 |
| 9,977,490 B2 * | 5/2018 | Jeong | B43K 1/01 |
| 2002/0183723 A1 | 12/2002 | Belef et al. | |
| 2005/0030285 A1 * | 2/2005 | Fu | G06F 3/03543 345/157 |
| 2005/0261582 A1 * | 11/2005 | Becker | A61B 8/06 600/437 |
| 2006/0084861 A1 * | 4/2006 | Blank | A61B 5/02007 600/423 |
| 2006/0084911 A1 * | 4/2006 | Belef | A61B 8/12 604/95.01 |
| 2007/0083111 A1 | 4/2007 | Hossack et al. | |
| 2007/0197963 A1 * | 8/2007 | Griffiths | A61M 5/007 604/97.01 |
| 2008/0146940 A1 * | 6/2008 | Jenkins | A61B 8/08 600/463 |
| 2009/0177183 A1 * | 7/2009 | Pinkernell | A61M 25/00 604/506 |
| 2010/0305442 A1 * | 12/2010 | Tierney | A61B 8/12 600/443 |
| 2011/0264194 A1 * | 10/2011 | Griswold | A61B 5/0031 623/1.15 |
| 2012/0179068 A1 * | 7/2012 | Leo | A61B 5/0084 600/587 |
| 2012/0195078 A1 * | 8/2012 | Levin | A61B 18/1233 363/50 |
| 2013/0072997 A1 * | 3/2013 | Sanders | A61N 1/36053 607/18 |
| 2013/0090552 A1 * | 4/2013 | Ramamurthy | A61B 5/06 600/424 |
| 2013/0096480 A1 * | 4/2013 | Han | A61M 1/3653 604/5.04 |
| 2013/0190726 A1 * | 7/2013 | Kesner | A61M 25/0105 604/510 |
| 2013/0211394 A1 * | 8/2013 | Fischer | A61B 18/02 606/28 |
| 2013/0304061 A1 * | 11/2013 | Chang | A61B 18/1492 606/41 |
| 2014/0209797 A1 * | 7/2014 | Klimovitch | G01B 11/16 250/227.14 |
| 2014/0221897 A1 * | 8/2014 | Szamosfalvi | A61M 1/3672 604/6.07 |
| 2014/0263802 A1 * | 9/2014 | Tanigawa | B29C 53/602 242/473.6 |
| 2014/0276603 A1 * | 9/2014 | Magee | A61M 25/00 604/508 |
| 2014/0343433 A1 * | 11/2014 | Elbert | A61B 8/54 600/467 |
| 2014/0343434 A1 * | 11/2014 | Elbert | A61B 8/445 600/467 |
| 2016/0317120 A1 * | 11/2016 | Elbert | A61B 8/54 |

FOREIGN PATENT DOCUMENTS

| | | |
|---|---|---|
| JP | 2011512961 A | 4/2011 |
| JP | 2012050706 A | 3/2012 |

OTHER PUBLICATIONS

International Patent Application No. PCT/US2013/040958, International Search Report and Written Opinion dated Feb. 10, 2014, 9 pages.
International Patent Application No. PCT/US2013/040958, International Preliminary Report on Patentability dated Apr. 29, 2015, 20 pages.

* cited by examiner

SYSTEM AND METHOD FOR MONITORING DEVICE ENGAGEMENT

This application is a continuation of U.S. patent application Ser. No. 13/894,045, filed May 14, 2013, the entire contents of which are incorporated herein by reference.

TECHNICAL FIELD

This disclosure relates to an intravascular ultrasound (IVUS) system and a method of operating the same.

BACKGROUND

IVUS involves one or more ultrasound transducers emitting ultrasound energy based on received electrical signals and sending return electrical signals based on ultrasound energy reflected by various intravascular structures. IVUS is often used to generate images. In some instances, a console with a high-resolution display is able to display IVUS images in real-time. In this way, IVUS can be used to provide in-vivo visualization of the vascular structures and lumens, including the coronary artery lumen, coronary artery wall morphology, and devices, such as stents, at or near the surface of the coronary artery wall. IVUS imaging may be used to visualize diseased vessels, including coronary artery disease. In some instances, the ultrasound transducer(s) can operate at a relatively high frequency (e.g., 10 MHz-60 MHz, in some preferred embodiments, 40 MHz-60 MHz) and can be carried near a distal end of an IVUS catheter. Some IVUS systems involve mechanically rotating the IVUS catheter for 360-degree visualization.

Many IVUS systems are configured to perform pullback operations, in which imaging components of the catheter are translated through the coronary arteries of a patient while acquiring images. The result is a 360-degree image with a longitudinal component. When performing a pullback operation, however, it can important that components of the IVUS system are secured properly to assure that the proper components translate relative to others. When components are not secured properly, the pullback operation may not yield the desired results. Moreover, when a pullback operation fails, the IVUS system operator is often left unaware that a pullback operation is not working until after it has been performed, and even then, may not be sure why the pullback operation did not work appropriately.

SUMMARY

Embodiments discussed in this disclosure can ensure that an IVUS catheter is properly anchored to other IVUS equipment before enabling performance of certain IVUS operations. Embodiments of the system can include a catheter for inserting into the vasculature of a patient, the catheter comprising a transducer for producing and receiving ultrasound signals that can be constructed into an ultrasound image. Some IVUS system embodiments may include a translation mechanism that includes an anchor port for anchoring the catheter, and circuitry configured to provide a first output corresponding to engagement between the catheter and the anchor port of the translation mechanism. The circuitry can include a sensor, such as an optical switch, that detects engagement between the catheter and the translation mechanism. In some instances, the circuitry can include digital circuitry, and the first output can include a digital signal.

Some embodiments can include a controller configured to determine via the first output if the IVUS catheter is engaged with the anchor port of the translation mechanism. The controller can then place the translation mechanism in a connected mode or disconnected mode based on whether or not the catheter is anchored to the translation mechanism. If the translation mechanism is in the connected mode, the controller can enable certain operations of the IVUS system that are otherwise disallowed if the translation mechanism is in the disconnected mode. Such allowable operations can include imaging operations and accessing information stored in memory, which may be located in the catheter. In some embodiments, the system can include a display configured to indicate if the translation mechanism is in the connected mode.

The translation mechanism of the IVUS system, according to some embodiments, can include a patient interface module (PIM) and a linear translation system (LTS). The PIM can engage the catheter and can be secured to the LTS. The LTS can then translate the PIM with the secured catheter to perform a pullback operation. The transducer can be translated inside the catheter to acquire a longitudinal image. In some embodiments, pullback can be allowed or disallowed depending on the connection state between the catheter and the translation mechanism. The anchor port on the translation mechanism can be located on the LTS, while the PIM may be placed in connected or disconnected mode based upon the engagement status of the LTS and the catheter.

The details of one or more examples are set forth in the accompanying drawings and the description below. Other features, objects, and advantages will be apparent from the description and drawings, and from the claims.

DETAILED DESCRIPTION

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
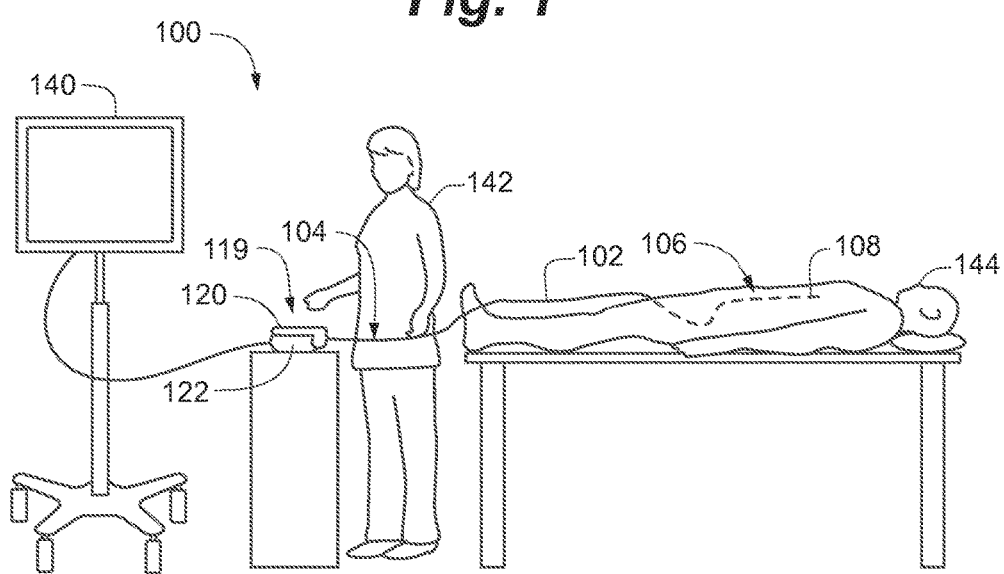
FIG. 1 is an illustrative embodiment of an IVUS system.

FIG. 1 is an illustrative embodiment of an IVUS system 100. The IVUS system 100 of FIG. 1 includes a catheter 102 having a proximal end 104 and a distal end 106 for inserting into an artery of a patient 144 for imaging. The catheter 102 may be inserted into the patient 144 via the femoral artery, for example. In FIG. 1, broken lines represent portions of the catheter 102 inside the patient's 144 body. According to certain embodiments, the catheter 102 can include a transducer 108 at or near its distal end 106. To perform an imaging function, the transducer 108 can emit ultrasound pulses. The ultrasound pulses can then reflect off the tissue of a patient 144 and can be detected by the transducer 108, which can convert the reflected ultrasound pulses into an electrical signal for image construction. Accordingly, an integrated ultrasound generator may be included in the IVUS system.

The IVUS system 100 of FIG. 1 also includes a translation mechanism. As shown, the translation mechanism 119 includes a patient interface module (PIM) 120 and a linear translation system (LTS) 122. The LTS can be mechanically engaged with the catheter 102. The LTS can be configured to translate the catheter 102 a controlled distance within the patient 144 during a pullback or other translation operation. In this embodiment, the PIM 120 of the translation mechanism 119 also acts as an interface with the catheter 102.

The IVUS system 100 can include a user interface 140 that can receive commands by a system user 142 and/or display IVUS data acquired from the catheter 102 (e.g., as IVUS images). The user interface 140 may include a traditional PC with software configured to communicate with the other components of the IVUS system 100. In some embodiments, the user interface 140 may include a display configured to display system information and/or IVUS signals from the catheter 102 (e.g., as IVUS images). In some embodiments, the user interface 140 can include a touchscreen display, which can act to both receive commands from a system user 142 and display IVUS data from the catheter 102. In some embodiments, the user interface 140 can include an imaging engine configured to construct images from the IVUS data provided by the catheter 102, such as ultrasound signals provided by the transducer 108. In some embodiments, the user interface 140 can include or be in communication with the ultrasound generator.

Figure 2:
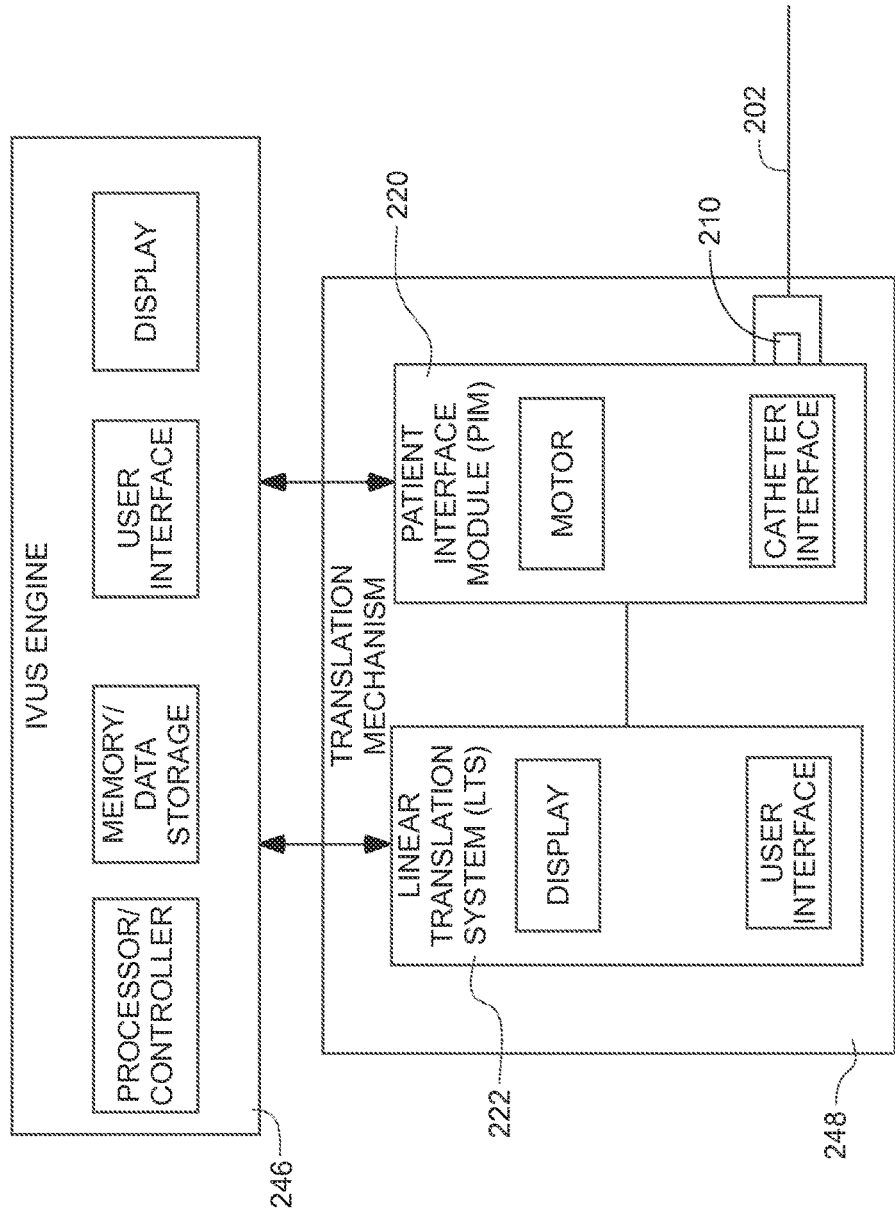
FIG. 2 is a block diagram of an embodiment of the IVUS system.

FIG. 2 is a block diagram of an IVUS system embodiment. In some embodiments, the IVUS engine 246 (e.g., an imaging engine) can include a processor/controller, memory/data storage, a user interface, and a display (among other possible components). These components may be integrated into, for example, a touch screen display and/or a computer. The IVUS engine 246 can generally be in communication with a translation mechanism 248, configured to translate the catheter 202 or a portion of the catheter 202. The translation mechanism 248 can, in some embodiments, include its own display and user interface. The translation mechanism 248 and user interface can allow the translation mechanism 248 to be used in a manual mode without requiring operating instructions from the IVUS engine 246. In some embodiments, the translation mechanism 248 can include a motor that can be used to adjust the position of the transducer at the distal end of the catheter 202 rotationally and/or translationally.

In some embodiments, the translation mechanism 248 can include a linear translation system (LTS) 222. The LTS 222 can include the aforementioned display and interface for allowing manual operation of the translation mechanism 248. In some embodiments, the translation mechanism 248 can include a patient interface module (PIM) 220. The PIM 220 can include a catheter interface, which can be attachable to the catheter 202. In some embodiments, the PIM 220 can include the aforementioned motor for adjusting the position of the transducer at the distal end of the catheter 202. According to some embodiments, a translation mechanism 248 can include both a PIM 220 and an LTS 222. In such embodiments, the PIM 220 and the LTS 222 may be fixedly attached to one another. The PIM 220 and LTS 222 may be in communication with one another, and may each individually be in communication with the IVUS engine 246.

In some embodiments of the IVUS system, the transducer on the distal end of the catheter 202 can rotate and/or translate. Rotation of the catheter 202 can be full 360-degree rotation to allow 360-degree imaging of a location such as a patient's artery. In some embodiments, the catheter can be an array catheter, in which rotation need not be necessary for such 360-degree imaging. Translation of the catheter 202 can allow imaging of multiple locations along the artery. Sequential scans can be performed at multiple translation positions to form an aggregate longitudinal image. In some embodiments, the catheter 202 can include a drive cable, which contains an electrical transmission line and is coupled to the transducer. In some embodiments, the catheter 202 can include a sheath defining a lumen within which the transducer and the drive cable are allowed to move freely. Thus, in some embodiments, the transducer can both translate and rotate within the sheath via the drive cable without the sheath moving within the artery. This can be advantageous to avoid excess friction between the catheter and the interior of a patient's artery as the transducer is moved during imaging or other IVUS operations. For example, while moving inside the sheath, the catheter does not drag along vessels which may have plaques prone to rupture.

According to some embodiments of the IVUS system, the catheter 202 can include catheter memory 210. Thus, if the catheter 202 is removed from the system, the catheter memory 210 can remain with the catheter 202. This way, information that is deemed important to a specific catheter 202 can be kept with that particular catheter 202. In certain embodiments, the catheter memory 210 is located on the proximal end of the catheter 202. In some embodiments, the catheter memory 210 can contain information specific to the catheter 202, such as the model of the catheter 202. In some embodiments, the catheter memory 210 can contain information about the particular components within the catheter 202, such as information about the transducer. Such transducer information can include the frequency response of the transducer, its date of assembly, gain, output level, number of times mated to the IVUS system, and/or other transducer-specific information. In some embodiments, the catheter memory 210 can store usage information concerning the catheter 202 and/or the transducer, such as usage time, date, duration, and/or information regarding the patient in which the catheter 202 was used. In some instances, storing such information in the catheter memory 210 can guarantee that this information is associated with the correct catheter 202, and/or that the IVUS engine 246 can detect this information upon catheter 202 engagement or upon the engine 246 requesting such information.

As mentioned, for some IVUS operations, the transducer can be translated along a length of an artery. To facilitate such a measurement, some embodiments of the IVUS system include a translation mechanism 248. The translation mechanism 248 can engage the catheter 202 and enable the operator of the IVUS system to translate the transducer within the catheter 202 in a specific way. Among various embodiments of the IVUS system, the translation mechanism 248 can translate the catheter 202 a desired distance, at a desired speed, or optionally both. Movement of the transducer can be initiated from the translation mechanism 248 directly and/or from an external controller such as the IVUS engine 246. In the case of an external controller, translation may be performed manually by a user or may be part of an automated process.

In some embodiments of the IVUS system, the translation mechanism 248 can include a PIM 220 and an LTS 222. In some embodiments, the PIM 220 can be configured to attach to the proximal end of the catheter 202. This attachment can include both an electrical and a mechanical attachment. For example, in some embodiments, the PIM 220 can provide the mechanical interface to secure the catheter 202, as well as the mechanical energy to rotate the transducer within the catheter 202. In some embodiments, the PIM 220 can provide the electrical interface that transmits the signal from the integrated ultrasound generator to the catheter 202 and receives the return signal. As such, in some embodiments, the PIM 220 can provide the electromechanical interface between the catheter 202 and the IVUS engine 246.

According to some embodiments, the PIM 220 can be configured to mate to the LTS 222. The LTS 222, while mated with the PIM 220 and catheter 202, can provide longitudinal translation of the transducer. In many embodiments, the longitudinal translation of the transducer can involve pullback of the catheter imaging core at a controlled rate. The LTS 222 can provide calibrated linear translation for acquisition of longitudinal IVUS data (e.g., for imaging). The LTS 222 may feature a display. The display may indicate the linear distance traversed and/or the translation speed. In some embodiments, the display may include controls for starting/stopping translation, setting translation speed, resetting linear distance traversed to zero, switching to manual mode, and so on. In some embodiments, in manual mode, the IVUS system operator can freely move the catheter imaging core forward and backward.

Figure 3:
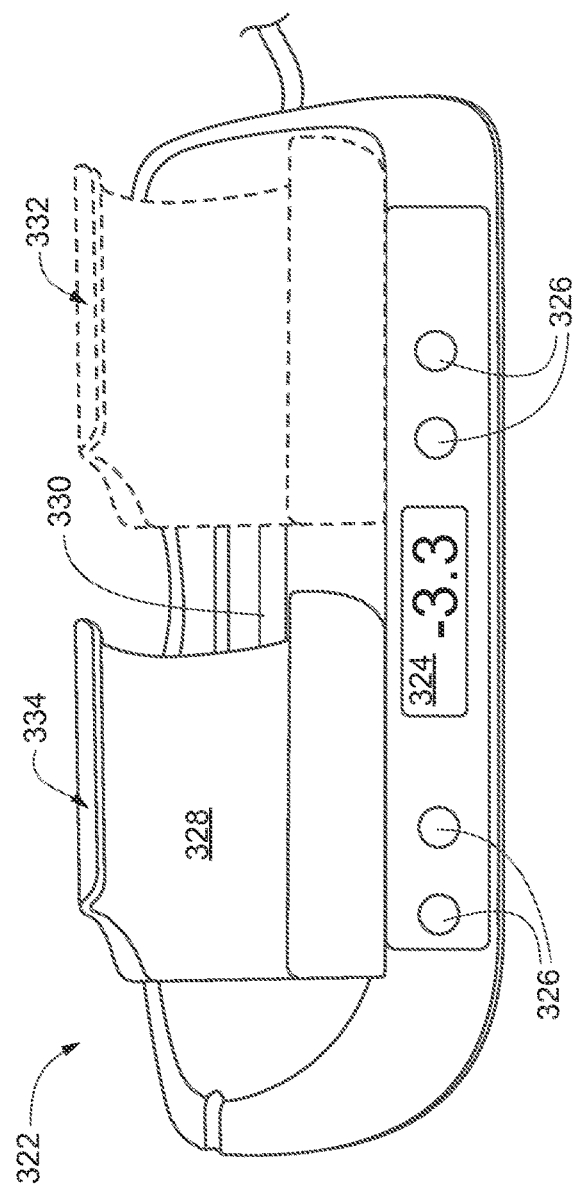
FIG. 3 is a view of an embodiment of a linear translation system according to certain embodiments of the invention.

FIG. 3 shows an embodiment of an LTS 322 according to certain embodiments of the invention. The LTS 322 can include a display 324 and controls 326 for user observation and manipulation of settings on the LTS 322. The LTS 322 can include a cradle 328 that may be configured to mate with a PIM. In some embodiments, the cradle 328 can translate along a track 330. In some such embodiments, when a catheter is coupled to a PIM, and the PIM is mated with the cradle 328, the LTS 322 can translate a transducer carried by the catheter in a desired manner by translating the cradle 328 along the track 330. The cradle 328 of FIG. 3 is shown in two possible positions—a distal position 334, shown in solid lines, and a proximal position 332, shown in phantom. In many embodiments, the LTS 322 can translate the cradle 328 from the distal position 334 to the proximal position 332 in a pullback operation. It should be appreciated that in some IVUS operations, the LTS 322 can be configured to translate between the distal position 334 and the proximal position 332 in either direction and/or to stop anywhere in between along the track 330.

In some embodiments, because of the translating ability of the LTS, longitudinal translation of an IVUS transducer can be performed manually by the IVUS system operator or under motorized control. Motorized longitudinal translation can enables the acquisition of calibrated three-dimensional volume data. This can allow the IVUS engine to accurately measure distances along the length of the artery under investigation, as well as the imaging of multiple regions of interest in a single procedure by advancing or retracting the IVUS assembly without moving the catheter sheath.

Figure 4:
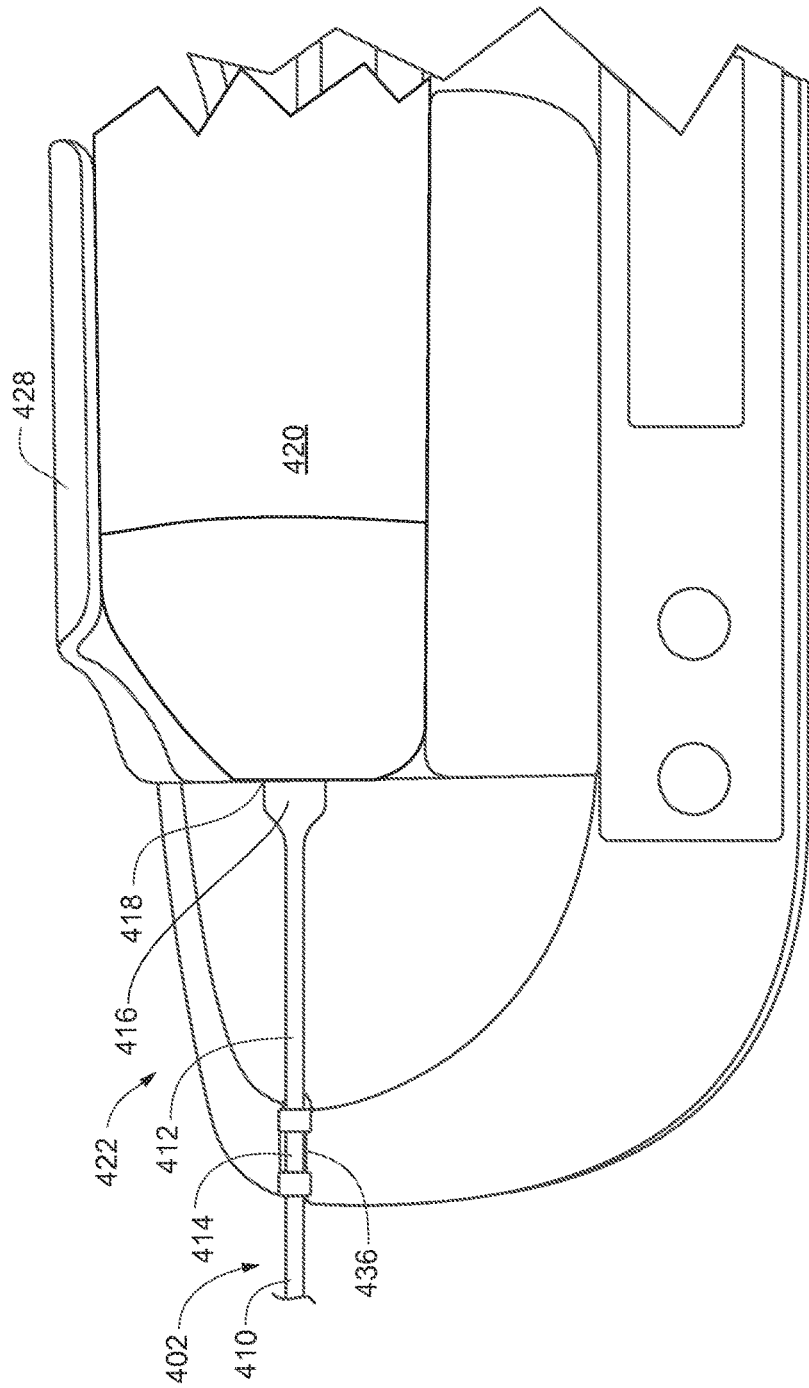
FIG. 4 shows the coupling of a catheter, a PIM, and an LTS according to some embodiments of the invention.

FIG. 4 shows an illustrative coupling of a catheter 402, a PIM 420, and an LTS 422 according to some embodiments of the invention. The proximal end of the catheter 402 can include a connector 416 that attaches to the PIM 420. In some embodiments, the connector 416 can secure the connection between the catheter 402 and the PIM 420 at catheter interface 418. In some embodiments, the connector 416 can provide an electrical and mechanical interface to the catheter 402 from the IVUS system. The PIM 420 may rest in the cradle 428 of the LTS 422, which can secure the PIM 420 during translation operations such as pullback. The catheter 402 can include an anchor assembly 414. The LTS 422 can include an anchor port 436. In some embodiments, the anchor port 436 can be configured to receive the anchor assembly 414 of the catheter 402.

In many instances, when the PIM 420 is secured to the LTS 422, the drive cable 412 of the catheter 402 can be connected to the PIM 420, and the anchor assembly 414 of the catheter 402 can be anchored to the anchor port 436 of the LTS 422. In many such instances, a translation operation (such as a pullback operation) may be performed. A transducer carried by the drive cable 412 can be positioned within a patient's vessel at a location distal to an area of interest. The LTS 422 can translate the cradle 428 from a distal position to a proximal position along a track, thereby translating the transducer from its initial location across the area of interest. While the PIM 420 is translating with the drive cable of the catheter 402 secured, the transducer in the catheter 402 translates with it. Thus, longitudinal IVUS measurements may be made by the transducer, interfacing with the IVUS engine via the PIM 420. When the anchor assembly 414 of the catheter is anchored to the anchor port 436 of the LTS 422, the sheath 410 of the catheter 402 can be held in place while the transducer is translating and optionally rotating within it. Thus, a pullback operation (or other translation operation) can be performed while ensuring that the sheath 410 does not slide within the patient's vasculature.

In some embodiments, it can be important to ensure that the catheter 402 is properly engaged to the LTS 422. As noted, in some embodiments, the catheter 402 can engage the LTS 422 by the anchor assembly 414 of the catheter 402 being anchored to the anchor port 436 of the LTS 422. Knowing that the catheter is anchored to the LTS suggests that the system is in a configuration conducive to performing certain measurements. Thus, it can be advantageous to prevent some IVUS operations if the catheter 402 is not properly anchored to the LTS 422. To do so, some embodiments of the IVUS system include a sensor configured to sense the engagement between the catheter 402 and the LTS 422. Some such embodiments can sense the anchoring of the anchor assembly 414 of the catheter 402 to the anchor port 436 of the LTS 422. In some embodiments, if the sensor does not sense the engagement between the catheter 402 and the LTS 422, certain operations of the IVUS system are disabled.

Figure 5:
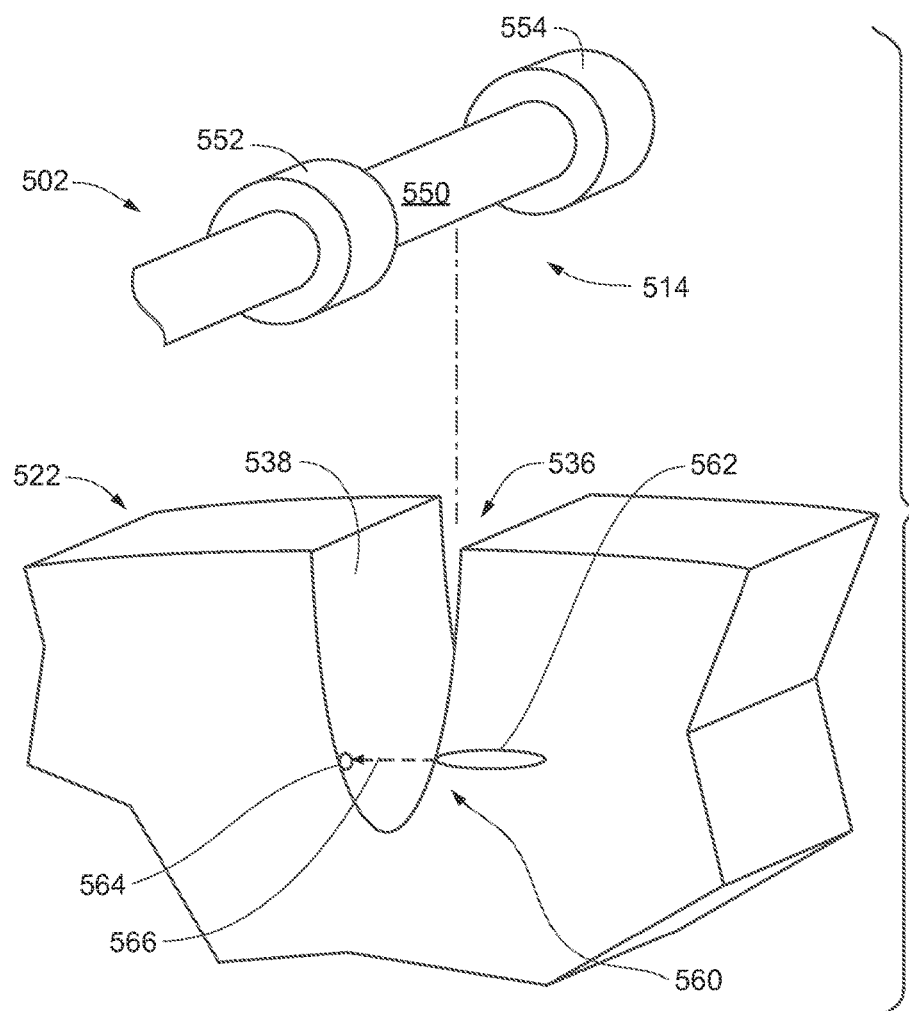
FIG. 5 is a perspective view of the anchor port of the LTS according to certain embodiments of the invention.

FIG. 5 shows an illustrative anchor port 536 of the LTS 522 according to certain embodiments of the invention. The anchor port 536 can include a notch 538 in the surface of the LTS 522. A portion of the anchor assembly 514 of the catheter 502 can be inserted into the notch 538. The anchor assembly 514 can include a center portion 550, a first stopping portion 552 and a second stopping portion 554. In preferred embodiments, the stopping portions 552, 554 are larger in diameter than the center portion 550. It should be appreciated that in some embodiments, a single stopping portion could be used.

In the illustrated embodiment, the center portion 550 of the anchor assembly 514 is received by the notch 538 in the LTS 522. Once received, stopping portions 552, 554 act to prevent the anchor assembly 514 from translating in a direction substantially along the longitudinal axis of the anchor assembly 514, which in some embodiments, is the direction of pullback during operation of the IVUS system. It will be appreciated that the configuration of anchor assembly 550 and anchor port 536 in FIG. 5 is merely exemplary, and that many other complementary anchor assembly and anchor port arrangements that function to prevent axial translation of the anchor assembly.

The anchor port of FIG. 5 can include a sensor 560 that is configured to detect the presence of the anchor assembly 514 in the anchor port 536. The sensor 560 can be a mechanical switch, a pressure sensor, an optical switch, or other suitable sensor. FIG. 5 shows one embodiment. The sensor 560 can be an optical switch that includes a photo emitter 562 and a photo detector 564 arranged on either side of the notch 538. The photo emitter 562 can emit electromagnetic radiation 566 toward the photo detector 564, which detects the radiation 566. However, when the electromagnetic radiation is blocked from the photo detector 564 by, for example, the anchor assembly 514, the photo detector 564 no longer senses the radiation 566. Thus, the optical switch arrangement can be used to detect the presence of an object within the notch 538, such as the anchor assembly 514 of the catheter 502. It should be noted that, while in FIG. 5 the optical switch is shown as being at the near edge of the notch 538, the location of the sensor may be substantially in the center of the notch 538, or at any other desired location as long as the anchor assembly 514 sufficiently blocks the electromagnetic radiation from reaching the photo detector 564 from the photo emitter 562 when engaged with the anchor port 536. In some configurations, the sensor can include a mechanical switch such as a lever such that when the anchor assembly 514 of the catheter 502 is sufficiently inserted into the anchor port 536, it depresses the lever to indicate the engagement of the two. The lever may act to open or close a circuit when depressed, for example.

Figure 6:
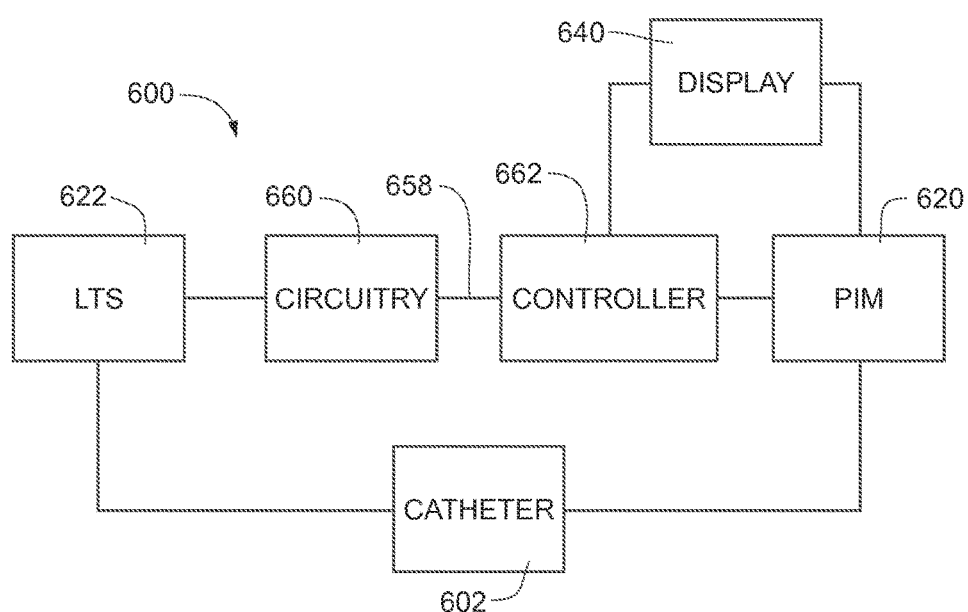
FIG. 6 is a system level block diagram showing an embodiment of an IVUS system comprising a controller.

In some embodiments, the sensor 560 of FIG. 5 can be implemented into circuitry 660 as shown in FIG. 6. FIG. 6 is a system level block diagram showing such an embodiment of an IVUS system, further comprising a controller. Some embodiments of the IVUS system can include circuitry 660 configured to provide a first output signal 658. The first output signal 658 can corresponds to engagement between the catheter 602 and the translation mechanism. In some embodiments, the engagement may include the anchoring of the anchor assembly of the catheter 602 into the anchor port of the LTS 622. The circuitry 660 may include a switch (e.g., an optical switch) or other sensor to produce the first output 658.

In some embodiments, the circuitry 660 can include digital circuitry. The digital circuitry can provide via the first output 658 a first signal or a second signal depending on the engagement status between the catheter 602 and the translation mechanism (e.g. if the catheter 602 is or is not anchored to the LTS 622). In some embodiments, the circuitry 660 can include analog circuitry. In such embodiments, engagement between the catheter 602 and the translation mechanism can be determined by the analog output crossing a threshold value. According to various embodiments of the invention, crossing a threshold may occur from either above or below the threshold in order to indicate engagement.

The IVUS system 600 of FIG. 6 includes a catheter 602 that is coupled to the LTS 622. Circuitry 660 can provide a first output 658 to the controller 662 depending on the engagement status of the catheter 602 and the translation mechanism. In some embodiments, such as the one shown in FIG. 6, the engagement status can relate to the engagement of the catheter 602 and the LTS 622. In some embodiments, the controller 662 can measure the first output 658 directly. In some embodiments, an additional component may measure the first output 658 and signal the controller 662.

In some embodiments, the controller 662 can place the translation mechanism or a portion thereof in a connected mode if the IVUS catheter 602 is anchored to a portion of the translation mechanism or in a disconnected mode if the IVUS catheter 602 is not. In some embodiments, the controller 662 can be configured to enable the performance of an IVUS operation if the translation mechanism or portion thereof is in the connected mode but not enable the operation if it is in the disconnected mode.

In the illustrated embodiment of FIG. 6, the controller 662 can place the PIM 620 in a connected or disconnected mode based upon whether or not the catheter 602 is appropriately engaged to the LTS 622, as determined via the first signal 658. After determining the engagement status, the controller 662 can communicate with the PIM 620, placing it in a connected or disconnected mode based upon the output 658.

In some embodiments, the IVUS system 600 can receive a command to perform an IVUS operation or task via a user interface or some other interface for receiving commands. Upon receiving the command, the IVUS system 600 can determine whether or not the IVUS catheter 602 is anchored to the LTS 622 and can place the PIM 620 in the connected or disconnected mode, accordingly. In some embodiments, the IVUS system 600 and/or PIM 620 can be in the connected mode or the disconnected mode before receiving the command to perform an IVUS operation or task. In many embodiments, if the PIM 620 is in the connected mode, the IVUS task can be carried out as commanded. In many embodiments, if the PIM 620 is in the disconnected mode, the IVUS system 600 can refuse to carry out the commanded IVUS task.

In some embodiments, the IVUS operation or task that can be enabled or disabled based on the mode of operation includes at least one of an imaging and a memory access operation. In some embodiments, the memory access operation can include accessing information stored in memory contained in the IVUS catheter 602. The enabled or disabled IVUS operation may additionally or alternatively include a pullback operation, in which the translation mechanism (e.g., the PIM 620 and the LTS 622) causes retraction of an IVUS transducer carried by the IVUS catheter 602 by a given distance, or any such task translating an IVUS transducer in the proximal direction of the IVUS catheter 602.

In some embodiments, the IVUS system 600 can include a display 640. The display 640 can be configured to indicate if the translation system, including a part thereof such as the PIM 620, is in the connected mode. It should be appreciated that indicating if the translation system, or particularly the PIM, for example, is in the connected mode can include many options. For example, some embodiments of the system can display a "not connected" message if proper engagement is not detected. In such an embodiment, the lack of a "not connected" message may constitute indicating that the system is in the connected mode. Some embodiments of the invention may be configured to display a "connected" message if adequate engagement is detected. Not displaying the "connected" message may constitute an indication that the translation system is in the disconnected mode. Other embodiments can display both "connected" and "disconnected" messages for indication to the user. With further regard to FIG. 6, in such embodiments comprising a display 640, the display 640 may be in communication with the controller 662 and/or the PIM 620 in order to display desired information. For example, the controller 662 may signal to the display 640 to indicate whether or not the translation mechanism is in the connected mode, while the PIM 620 may send IVUS imaging signals from the catheter 602 to the display 640.

Figure 7:
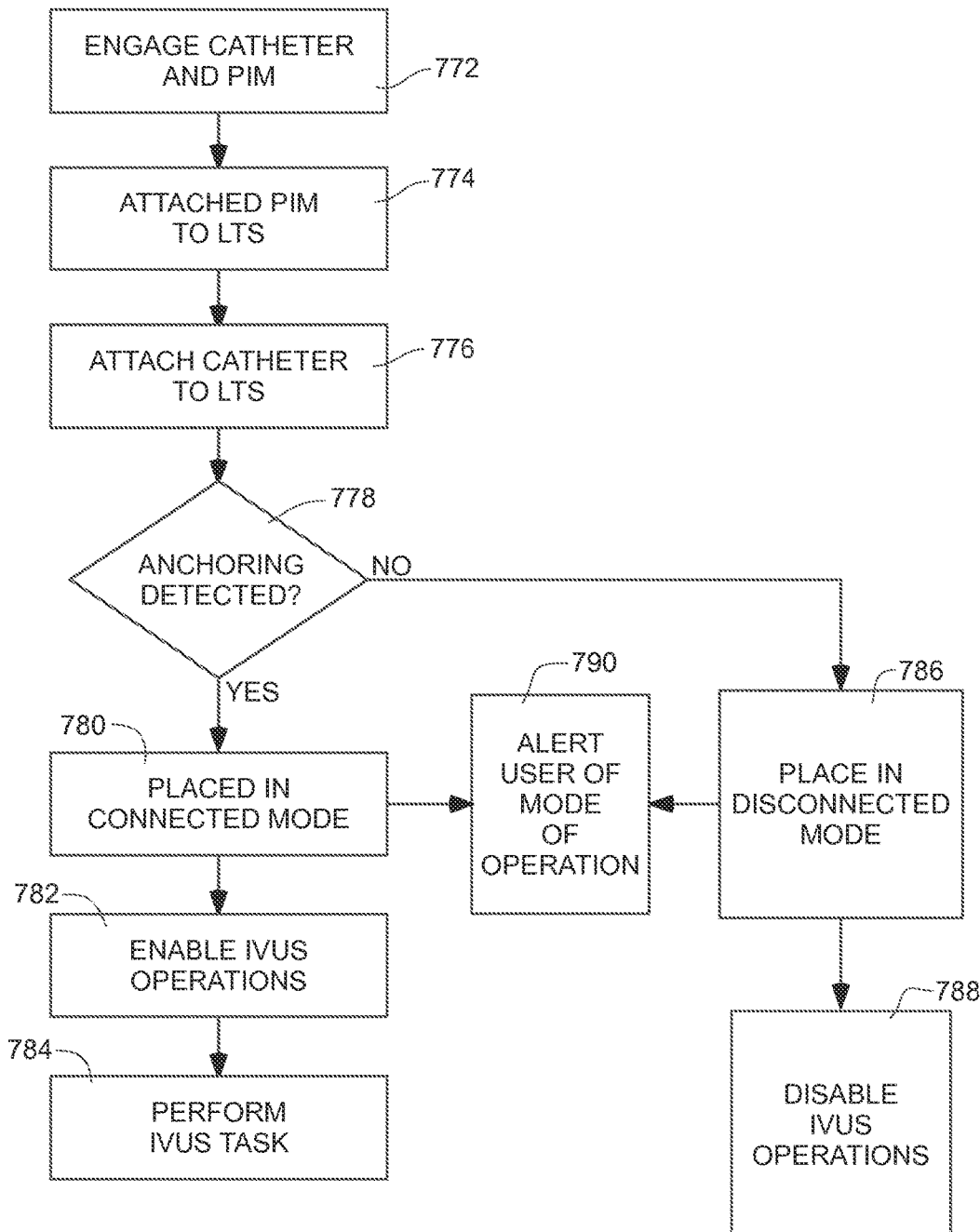
FIG. 7 is a process-flow diagram illustrating operation of an embodiment of the IVUS system.

FIG. 7 is a process-flow diagram illustrating operation of an embodiment of the IVUS system. Like other IVUS systems discussed in this disclosure, the IVUS system of FIG. 7 can include a PIM, a catheter, and an LTS, each separate from one another. The catheter can be engaged with the PIM 772. The PIM can be attached to the LTS 774. The catheter can be attached to the LTS 776. In certain embodiments, attachment of the catheter to the LTS can include anchoring an anchoring assembly of the catheter to an anchor port of the LTS. As noted, such attachments and connections can be important in a variety of IVUS operations, such as imaging and/or pullback. In some embodiments, the IVUS system can determine if appropriate anchoring of the catheter has been detected 778. If it is, the system or components of the system can be placed in a connected mode 780 and, in some embodiments, the user can be alerted 790 of the connected mode of operation. This may be done via a display component of the system as described above and/or via any suitable audible or visible alert. Upon placing the system or component of the system in a connected mode, certain IVUS operations may be enabled 782. The IVUS system may then perform an IVUS task 784, such as a pullback longitudinal imaging measurement. Components of the system that can be placed into a connected mode include the PIM, the LTS, and the catheter, for example. Among various embodiments of the IVUS system, any combination of these or other components may be placed in connected mode.

If, on the other hand, it is determined that the catheter is not properly anchored to the LTS, the IVUS system or component of the IVUS system may be placed in a disconnected mode 786. Similarly to the connected mode discussed above, components or combinations of components such as the PIM, the LTS, and the catheter can be placed in disconnected mode. In disconnected mode, particular IVUS operations may be disabled 788. Disabled IVUS operations may include imaging operations, translation operations, and memory access operations, among others. In such a case, the user can be alerted of the disconnected mode of operation 790. As noted, this alert may be done via a display component of the system as described above and/or via any suitable audible or visible alert. It should be appreciated that, while the process illustrated in FIG. 7 shows the steps in an illustrative sequence, this particular sequence does not define operation of all embodiments of the invention. Various steps may be modified among varying embodiments of the invention without sacrificing operability of the IVUS system.

Figure 8:
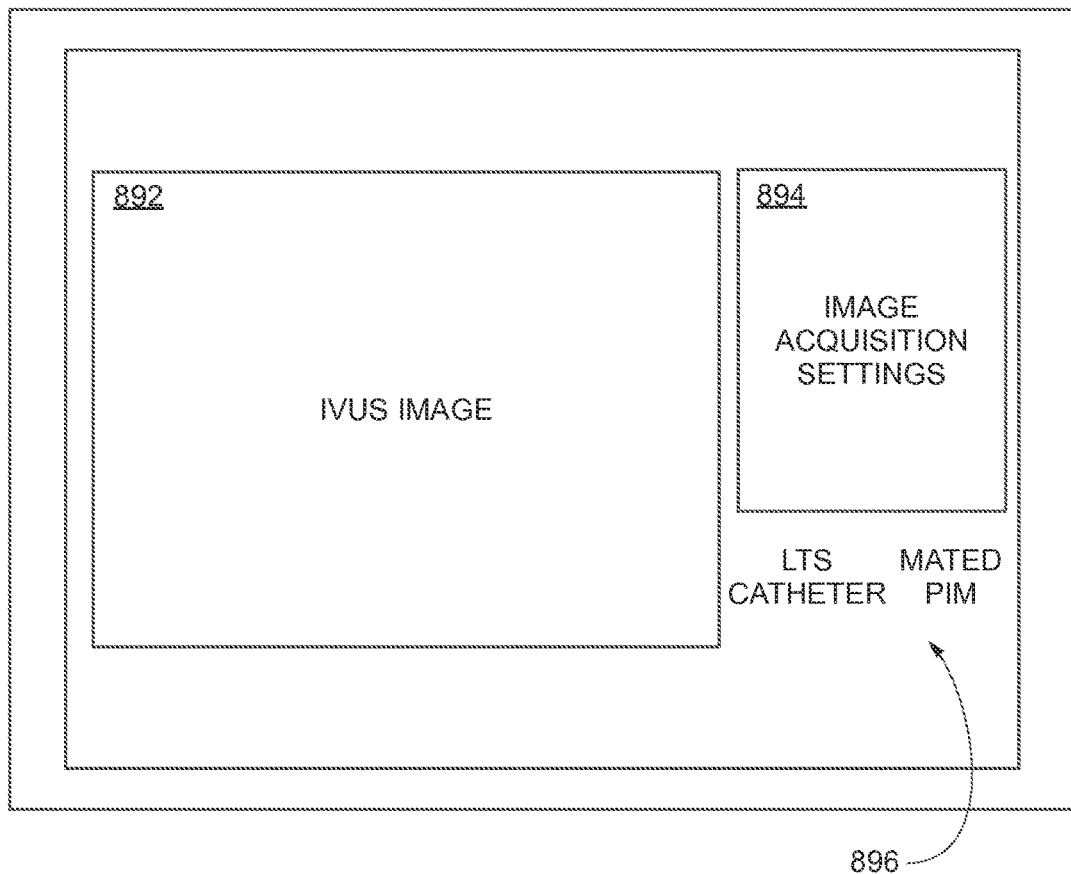
FIG. 8 is an exemplary block layout of a display used with certain embodiments of the IVUS system.

FIG. 8 is an exemplary block layout of a display 840 used with certain embodiments of the IVUS system. In some embodiments, the display 840 can display an IVUS image 892. The image may be a real-time image displayed during IVUS measurements. The image may be a stored image displayed upon recall from memory. During an imaging operation, the display 840 may further include a selection of image acquisition settings 894. Such settings may include zoom and gain settings to adjust while acquiring ultrasound images. These settings may be selected and adjusted via the user interface, which may include a touch screen or an additional external selection tool, such as a keyboard and/or a mouse. In some embodiments, the display 840 may further include connection indications 896, indicating to the user of the system which components are connected and operational. In some embodiments, the connection indications 896 can appear only when particular components are sensed as connected. For example, in FIG. 8, "LTS," "Catheter," and "PIM" are all shown, indicating each of these elements is sensed by the system. In, addition, the connection indications 896 section can include the indication "Mated," indicating that the catheter is anchored to a part of the translation mechanism, such as the LTS, and that operations requiring such engagement are enabled. As discussed, the indication of sufficient engagement of the catheter to the LTS, for example, can be done in a variety of ways, depending on the particular IVUS system, the context, and a variety of other factors.

It should be appreciated that components described with regard to particular embodiments of the invention may be combined to form additional embodiments. The techniques described in this disclosure may also be embodied in or encoded in a computer-readable medium, such as a non-transitory computer-readable storage medium containing instructions. Instructions embedded or encoded in a computer-readable storage medium may cause a programmable processor, or other processor, to follow the instructions prescribed. Computer readable storage media may include random access memory (RAM), read only memory (ROM), a hard disk, optical media, or other computer readable media.

Various examples have been described. These and other examples are within the scope of the following claims.

The invention claimed is:

1. An intravascular ultrasound (IVUS) system, comprising:
   an IVUS catheter comprising:
      a sheath,
      a drive cable extending through the sheath being coupled to an IVUS transducer at a distal end,
      a connector at a proximal end of the IVUS catheter, the connector being coupled to a proximal end of the drive cable, and
      an anchor assembly positioned near a proximal end of the sheath, the anchor assembly being separate from the connector of the IVUS catheter; and
   a translation mechanism comprising:
      a catheter interface configured to electrically and mechanically interface with the connector of the IVUS catheter,
      an anchor port separate from the catheter interface and configured to receive the anchor assembly of the IVUS catheter in order to anchor the anchor assembly of the IVUS catheter to the translation mechanism, and
      a sensor positioned proximate the anchor port, the sensor outputting a signal representative of whether or not the anchor assembly of the IVUS catheter is anchored to the anchor port of the translation mechanism to enable a controller to place the translation mechanism in a connected mode if the anchor assembly is anchored to the anchor port or in a disconnected mode if the anchor assembly is not anchored to the anchor port, wherein
   the translation mechanism is configured to translate the catheter interface relative to the anchor port.

2. The IVUS system of claim 1, wherein the sensor comprises an optical sensor.

3. The IVUS system of claim 2, wherein the anchor port comprises a notch formed in a portion of the translation mechanism, the notch having a first side and a second side opposite the first side, and wherein the optical sensor comprises a photo emitter positioned in the first side of the notch and a photo detector positioned in the second side of the notch such that, when the anchor assembly of the IVUS catheter is anchored to the anchor port of the translation mechanism, the anchor assembly blocks the light from the photo emitter from reaching the photo detector.

4. The IVUS system of claim 1, wherein the sensor comprises a mechanical switch.

5. The IVUS system of claim 1, further comprising the controller that is configured to determine whether to place the translation mechanism in the connected mode or in the disconnected mode.

6. The IVUS system of claim 5, wherein at least one IVUS operation is enabled when the translation mechanism is in the connected mode and is disabled when the translation mechanism is in the disconnected mode.

7. The IVUS system of claim 6, wherein the at least one IVUS operation comprises performing a pullback operation via the translation mechanism.

8. The IVUS system of claim 5, further comprising a display in communication with the controller and being configured to present a graphical representation, and wherein the presented graphical representation includes an indication representing whether or not the anchor assembly of the IVUS catheter is anchored to the anchor port of the translation mechanism.

9. The IVUS system of claim 1, wherein the IVUS catheter comprises a memory including catheter information, and wherein the controller communicates with the memory of the IVUS catheter via the connector and the catheter interface.

10. The IVUS system of claim 9, wherein the controller communicates with the memory of the IVUS catheter only if the anchor assembly of the IVUS catheter is anchored to the anchor port of the translation mechanism.

11. The IVUS system of claim 1, wherein the translation mechanism comprises a patient interface module (PIM) and a linear translation system (LTS), the LTS being configured to translate the PIM between distal and proximal positions, and wherein the anchor port of the translation mechanism is positioned on the LTS and the catheter interface of the translation mechanism is positioned on the PIM.

12. An intravascular ultrasound (IVUS) system comprising:
an anchor sensor;
an IVUS catheter having
 a sheath,
 a drive cable positioned within the sheath, the drive cable being coupled to an IVUS transducer at a distal end,
 a connector located at a proximal end of the drive cable, the connector being separate from the sheath, and
 an anchor assembly positioned near a proximal end of the sheath,
a translation mechanism comprising a catheter interface and an anchor port separate from the catheter interface, the translation mechanism being configured to translate the catheter interface relative to the anchor port, and wherein the catheter interface being configured interface with the IVUS catheter via the connector of the IVUS catheter, and wherein the anchor port being configured to engage with the IVUS catheter via the anchor assembly of the IVUS catheter; and
a controller in communication with the anchor sensor and configured to:
 measure a first output from the anchor sensor corresponding to engagement between the anchor assembly of the IVUS catheter and the translation mechanism;
 determine, via the first output, if the anchor assembly of the IVUS catheter is anchored to the anchor port of the translation mechanism;
 place the translation mechanism in a connected mode if the anchor assembly is anchored to the anchor port or in a disconnected mode if the anchor assembly is not anchored to the anchor port; and
 provide a signal to a user alerting the user if the translation mechanism is in the disconnected mode.

13. The IVUS system of claim 12, wherein providing the signal to the user alerting the user that the translation mechanism is in the disconnected mode comprises sounding an audible alarm.

14. The IVUS system of claim 12 further comprising a display, and wherein providing the signal to the user alerting the user if the translation mechanism is in the disconnected mode comprises indicating on the display that the anchor assembly is not anchored to the anchor port.

15. The IVUS system of claim 14, wherein the controller is configured to generate on the display information that includes a connection status of the anchor assembly and the anchor port.

16. The IVUS system of claim 12, wherein the anchor sensor comprises a sensor positioned proximate the anchor port, the sensor outputting a signal representative of whether or not the anchor assembly of the IVUS catheter is anchored to the anchor port of the translation mechanism.

17. The IVUS system of claim 16, wherein the sensor comprises an optical sensor and/or a mechanical switch.

18. A method of operating an intravascular ultrasound (IVUS) system that includes:
a translation mechanism comprising a catheter interface and an anchor port separate from the catheter interface, the translation mechanism being configured to translate the catheter interface relative to the anchor port, and
an IVUS catheter having
 a sheath including an anchor assembly positioned near a proximal end of the sheath, the anchor assembly being configured to engage the anchor port of the translation mechanism,
 a drive cable positioned within the sheath, the drive cable being coupled to an IVUS transducer at a distal end,
 a connector located at a proximal end of the drive cable, the connector being separate from the sheath and configured to provide an electrical and mechanical interface between the IVUS catheter and the catheter interface of the translation mechanism, and
 a sensor positioned proximate the anchor port, the sensor outputting a signal representative of whether or not the anchor assembly of the IVUS catheter is anchored to the anchor port of the translation mechanism, the method comprising:
receiving the signal output from the sensor;
determining if the anchor assembly of the IVUS catheter is anchored to the anchor port of the translation mechanism;
preventing one or more IVUS tasks of the IVUS system if the anchor assembly of the IVUS catheter is not anchored to the anchor port of the translation mechanism; and enabling one or more IVUS tasks of the IVUS system if the anchor assembly of the IVUS catheter is anchored to the anchor port of the translation mechanism.

19. The method of claim 18, wherein preventing one or more IVUS tasks comprises disabling an operation of the IVUS system.

20. The method of claim 18, wherein preventing one or more IVUS tasks comprises alerting a user that the anchor assembly of the IVUS catheter is not anchored to the anchor port of the translation mechanism.

* * * * *